US007148375B2

(12) United States Patent
Edwards et al.

(10) Patent No.: US 7,148,375 B2
(45) Date of Patent: *Dec. 12, 2006

(54) BRANCHED PRIMARY ALCOHOL COMPOSITIONS AND DERIVATIVES THEREOF

(75) Inventors: Charles Lee Edwards, Houston, TX (US); Kirk Herbert Raney, Houston, TX (US); Paul Gregory Shpakoff, Houston, TX (US)

(73) Assignee: Shell Oil Company, Houston, TX (US)

( * ) Notice: Subject to any disclaimer, the term of this patent is extended or adjusted under 35 U.S.C. 154(b) by 247 days.

This patent is subject to a terminal disclaimer.

(21) Appl. No.: 10/817,640

(22) Filed: Apr. 2, 2004

(65) Prior Publication Data

US 2004/0198628 A1 Oct. 7, 2004

Related U.S. Application Data

(62) Division of application No. 10/679,174, filed on Oct. 3, 2003, now Pat. No. 6,909,020, which is a division of application No. 10/025,080, filed on Dec. 19, 2001, now Pat. No. 6,706,931.

(60) Provisional application No. 60/257,670, filed on Dec. 21, 2000.

(51) Int. Cl.
*C07C 309/00* (2006.01)
(52) U.S. Cl. .................. 562/36; 562/110; 562/111; 568/671
(58) Field of Classification Search .................. 562/36, 562/110, 111; 568/671, 672, 840
See application file for complete search history.

(56) References Cited

U.S. PATENT DOCUMENTS

| 2,778,855 | A | 1/1957 | Shokal et al. ................. 260/613 |
| 2,808,442 | A | 10/1957 | Smith et al. ................. 260/611 |
| 2,816,932 | A | 12/1957 | Di Nardo et al. ............ 260/615 |
| 3,058,805 | A | 10/1962 | Weber .......................... 23/113 |
| 3,130,007 | A | 4/1964 | Breck ........................... 23/113 |
| 3,308,069 | A | 3/1967 | Wadlinger et al. ........... 252/455 |
| 3,420,875 | A | 1/1969 | Di Salvo et al. ............. 260/513 |
| 3,428,654 | A | 2/1969 | Rubinfeld et al. ........... 260/327 |
| 3,462,525 | A | 8/1969 | Levinsky ...................... 424/56 |
| 3,506,580 | A | 4/1970 | Rubinfeld et al. ........... 252/138 |
| 3,524,864 | A | 8/1970 | Rubinfeld et al. ........... 260/327 |
| 3,579,537 | A | 5/1971 | Rubinfeld et al. ........... 260/327 |
| 3,676,523 | A | 7/1972 | Mason .............. 260/683.15 D |
| 3,686,351 | A | 8/1972 | Mason .............. 260/683.15 D |
| 3,702,886 | A | 11/1972 | Argauer et al. .............. 423/328 |
| 3,709,979 | A | 1/1973 | Chu ............................ 423/328 |
| 3,737,475 | A | 6/1973 | Mason .............. 260/683.15 D |
| 3,825,615 | A | 7/1974 | Lutz .................. 260/683.15 D |
| 3,832,449 | A | 8/1974 | Rubin et al. |
| RE28,341 | E | 2/1975 | Wadlinger et al. ........... 208/120 |
| 3,875,202 | A | 4/1975 | Steckler ....................... 260/458 |
| 3,950,496 | A | 4/1976 | Ciric ........................... 423/328 |
| 3,972,983 | A | 8/1976 | Ciric ........................... 423/328 |
| 3,996,337 | A | 12/1976 | Stabenow et al. .......... 423/328 |
| 4,020,121 | A | 4/1977 | Kister et al. ........ 260/683.15 D |
| 4,021,447 | A | 5/1977 | Rubin et al. ............. 260/326.8 |
| 4,046,859 | A | 9/1977 | Plank et al. ................. 423/328 |
| 4,086,186 | A | 4/1978 | Rubin et al. ................. 252/430 |
| 4,226,637 | A | 10/1980 | Linden et al. .......... 106/308 Q |
| 4,247,416 | A | 1/1981 | Doherty et al. ............. 252/428 |
| 4,247,728 | A | 1/1981 | Rubin et al. ................. 585/467 |
| 4,287,166 | A | 9/1981 | Dwyer et al. ............... 423/325 |
| 4,317,938 | A | 3/1982 | Lutz ........................... 568/619 |
| 4,397,827 | A | 8/1983 | Chu ............................ 423/326 |
| 4,440,871 | A | 4/1984 | Lok et al. .................... 502/214 |
| 4,482,531 | A | 11/1984 | Kuehl ......................... 423/329 |
| 4,495,303 | A | 1/1985 | Kuehl .......................... 502/62 |
| 4,503,275 | A | 3/1985 | Harris et al. ................ 568/866 |
| 4,544,512 | A | 10/1985 | Hozumi et al. ............. 558/169 |
| 4,568,654 | A | 2/1986 | Valyocsik ..................... 502/62 |
| 4,619,818 | A | 10/1986 | Derogane et al. ........... 423/306 |
| 4,640,829 | A | 2/1987 | Rubin ......................... 423/328 |
| 4,647,442 | A | 3/1987 | Derouane et al. ........... 423/306 |
| 4,698,217 | A | 10/1987 | Valyocsik ............... 423/328 C |
| 4,721,816 | A | 1/1988 | Edwards ..................... 568/618 |
| 4,721,817 | A | 1/1988 | Edwards ..................... 518/618 |
| 4,814,514 | A | 3/1989 | Yokota et al. .............. 568/608 |

(Continued)

FOREIGN PATENT DOCUMENTS

DE 100 20 899 A1 10/2001

(Continued)

OTHER PUBLICATIONS

Tsujii, Kaoru: Okahashi, Kenjii; Takeuchi, Takashi., "Physicochemical properties of anion surfactants with poly(oxyalkylene) group in water," Tochigi Res. Lab., Kao Soap Co., Tochigi, Japan (1981), 30(9), pp. 566-572.*

(Continued)

*Primary Examiner*—Shailendra Kumar

(57) ABSTRACT

A detergent composition having cold water solubility and exhibiting high calcium tolerance can be produced from biodegradable branched ether derivative compositions derived from a branched ether primary alcohol represented by the formula:

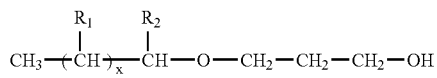

wherein $R_1$ represents hydrogen or a hydrocarbyl radical having from 1 to 3 carbon atoms, $R_2$ represents a hydrocarbyl radical having from 1 to 7 carbon atoms, x is a number ranging from 0 to 16, preferably from 3 to 13, wherein the total number of carbon atoms in the alcohol ranges from 9 to 24.

1 Claim, No Drawings

U.S. PATENT DOCUMENTS

| | | | | |
|---|---|---|---|---|
| 4,885,379 | A | | 12/1989 | Abend .......................... 558/34 |
| 4,931,218 | A | * | 6/1990 | Schenker et al. ........... 510/498 |
| 4,954,325 | A | | 9/1990 | Rubin et al. ................. 423/328 |
| 5,057,627 | A | | 10/1991 | Edwards ..................... 568/618 |
| 5,059,567 | A | | 10/1991 | Linsten et al. ................ 502/64 |
| 5,236,575 | A | | 8/1993 | Bennett et al. ............... 208/46 |
| 5,562,866 | A | * | 10/1996 | Hu et al. ..................... 510/432 |
| 5,912,408 | A | | 6/1999 | Trinh et al. ..................... 8/142 |
| 6,083,893 | A | | 7/2000 | Zint et al. ................... 510/221 |
| 6,087,311 | A | | 7/2000 | Van Dijk ..................... 510/294 |
| 6,100,433 | A | | 8/2000 | Dobert et al. ............... 568/678 |
| 6,153,574 | A | | 11/2000 | Janssen ...................... 510/224 |
| 6,159,920 | A | | 12/2000 | Ridyard ...................... 510/324 |
| 6,909,020 | B1 | * | 6/2005 | Edwards et al. ............ 568/671 |

FOREIGN PATENT DOCUMENTS

| | | | |
|---|---|---|---|
| EP | 0884298 A2 | | 12/1998 |
| GB | 1429143 | | 3/1976 |
| JP | 56115745 | | 9/1981 |
| JP | 03261779 | | 11/1991 |
| JP | 06073045 | | 3/1994 |
| JP | 10237497 | | 9/1998 |
| JP | 11-349507 | | 12/1999 |
| WO | WO 94/05761 | | 3/1994 |
| WO | WO 97/00843 | * | 1/1997 |
| WO | WO9932563 | | 7/1999 |
| WO | WO 99/42553 | | 8/1999 |

OTHER PUBLICATIONS

Myers, Drew, "Surfactant Science and Technology," pp. 82-85, VCH Publishers, Inc. (New York, NY, USA) 1988 (ISBN 0-89573-399-0).

K. Shinoda, "Principles of Solution and Solubility," translation in collaboration with Paul Becher, published by Mercel Dekker, Inc. 1978, pp. 292-304.

Reid, V.W., G.F. Longman and E. Heinerth, "Determination of Anionic-Active Detergents by Two-Phase Titration," *Tensile* 4, 1967, pp. 292-304.

B. E. Gordon, H. Roddewig and W. T. Shebs, "A Double Label Radiotracer Approach to Detergency Studies," Journal of American Oli Chemists' Society, vol. 44, No. 5 (1967) pp. 289-294.

W. T. Shebs and B. E. Gorden, "Improvements in Detergency Precision With Radioactive Soil," Journal of American Oil Chemists' Society, vol. 45, No. 5 (1968) pp. 377-380.

W. T. Shebs, "Radioisotope Techniques in Detergency," Chapter 3, *Detergency Theory and Technology*, Marcel Dekker, Inc., New York (1987) pp. 125-191.

Roger Hunter et al., "Allylation Using Allylborates," TETRAHEDRON, vol. 50, No. 3, 1994, pp. 871-888.

Birgit Bartels et al., "A Selectivity of Activated Ketal Reduction With Borane Dimethyl Sulfide," Journal of Organic Chemistry, vol. 58, No. 24, 1993, pp. 6756-6765.

T. Hosokawa et al., "Palladium (II)-Catalyzed Acetalization of Terminal Olefins Bearning Electron-Withdrawing Substituents With Optically Active Diols," Journal of Organic Chemistry, vol. 52, 1987, pp. 1958-1764.

F. Wang etal., Synlett, (1998) pp. 245-245.

A. A. Volkov et al., Dokl. Chem. 283, (1985), pp. 246-248.

International Search Report of Jul. 5, 2002.

U.S. Appl. No. 10/025,080, filed Dec. 19, 2001, Edwards et al.

CA: 120:107377 abs of Bulletin of the Chem. Soc. of Japan by Kuroda et al. 66 (8) pp. 2298-2303, 1993.

CA:1200:220779 abs of Tetrahedron by Piasecki et al. 40(23) pp. 4893-4896, 1984.

* cited by examiner

BRANCHED PRIMARY ALCOHOL COMPOSITIONS AND DERIVATIVES THEREOF

This is a division of application Ser. No. 10/679,174 filed Oct. 3, 2003 now U.S Pat. No. 6,909,020, the entire disclosure of which is hereby incorporated by reference which is a division of application Ser. No. 10/025,080 filed Dec. 19, 2001, now U.S. Pat. No. 6,706,931, the entire disclosure of which is hereby incorporated by reference which claims the benefit of U.S. Provisional Application No. 60/257,670 filed Dec. 21, 2000, the entire disclosure of which is hereby incorporated by reference.

FIELD OF INVENTION

This invention relates to a certain branched primary alcohol composition useful in producing detergent compositions.

BACKGROUND OF THE INVENTION

Nonionic and anionic surfactants are important constituents in many applications. Both aromatic and aliphatic sulfates and sulfonates are an important group of anionic surface-active agents used extensively in a number of industrial applications. These include operations in drilling for and recovery of crude oil; emulsifiers for pesticides used in crop protection; in shampoos and creams for personal care; bar soaps; laundry detergents; dishwashing liquids, hard surface cleaners; emulsifiers for emulsion polymerization systems; lubricants; wetting agents; and dispersants in a variety of specialized industrial applications.

The surfactants used in cleaning applications are designed to remove a wide variety of soils on fabrics and hard surfaces. Surfactants in this application have a balance of particulate soil removal and grease and oily soil removal characteristics. Especially in detergent compositions for cleaning fabrics, the surfactants used should have the ability to remove a broad spectrum of soil types.

In many cases, however, a surfactant which exhibits high detergency power will be poorly soluble in cold water. For example, surfactants present in laundry powder detergents should dissolve completely in a relatively short time interval under whatever wash temperature and agitation conditions are employed in the wash cycle chosen by the consumer. Undissolved detergent not only fails to provide cleaning benefits, but also may become entrapped in the laundry articles and remain behind as a residue either in the machine or on the garments themselves. The problem of dispersion and solubilization in the wash cycle are made worse under conditions of cold water washing especially at or below about 50° F. (10° C.). Lower wash temperatures are becoming ever increasing factors in today's wash loads as both energy conservation and increased use of highly colored, delicate fabrics lead to wash conditions that make powders difficult to dissolve.

In contrast to nonionic surfactants, which exhibit inverse solubility behavior and which, by virtue of hydrogen bridge bonds, show better solubility in cold water than in warm water, anionic surfactants show conventional behavior, i.e. their solubility increases more or less linearly with the temperature until the solubilized product is reached. The surfactant employed, whether anionic or nonionic, should be designed to remain homogeneous in the wash media at cold water washing temperatures to optimize the cleaning performance of the surfactant. Accordingly, surfactants with the ability to remove sebum types of soil and which have low Krafft point temperatures are desirable.

Surfactants which have good washing and cleaning performance have low Krafft temperatures. The Krafft temperature refers to the temperature at which the solubility of an anionic surfactant undergoes a sharp, discontinuous increase with increasing temperature. The solubility of an anionic surfactant will increase slowly with an increase in temperature up to the temperature point at which the solubility exhibits an extremely sharp rise. The temperature corresponding to the sharp rise in solubility is the Krafft temperature of anionic surfactant. At a temperature approximately 4° C. above the Krafft temperature, a solution of almost any composition becomes a homogeneous phase. Further, the Krafft temperature is a useful indicator of detergency performance because at and above the Krafft temperature, surfactants begin to form micelles instead of precipitates, and below the Krafft temperature point, surfactants are insoluble and form precipitates. At the Krafft point temperature, the solubility of a surfactant becomes equal to its critical micelle concentration, or CMC. The appearance and development of micelles are important since certain surfactant properties such as foam production depend on the formation of these aggregates in solution.

Each type of surfactant will have its own characteristic Krafft temperature point. In general, the Krafft temperature of a surfactant will vary with the structure and chain length of the hydrophobic hydrocarbyl group and hydrophilic portion of the molecule. Krafft temperature for ionic surfactants is, in general, known in the art. See, for example, Myers, Drew, Surfactant Science and Technology, pp. 82–85, VCH Publishers, Inc. (New York, N.Y., USA), 1988 (ISBN 0-89573-399-0), and K. Shinoda in the text "Principles of Solution and Solubility", translation in collaboration with Paul Becher, published by Marcel Dekker, Inc. 1978 at pages 160–161, each of which is incorporated by reference herein in its entirety.

A surfactant which exhibits a high Krafft point is generally insufficient in detergency and foaming power. Since the Krafft point is a factor having an influence on the surface activating capacities of a surfactant, at temperatures lower than the Krafft point, surface-activating capacities such as detergency, foaming power and emulsifying power begin to deteriorate, and the surfactant may precipitates on the fabric. Thus, the surfactant should desirably possess a low Krafft point, especially in light of current performance requirements in cold water washing temperatures.

However, even surfactants with good detergency and high cold water solubility limits, as shown by their low Krafft point temperatures, may nevertheless leave behind precipitates on the surface to be cleaned if the surfactant is not tolerant to the concentration of electrolytes (typically magnesium and calcium) present in the aqueous washing medium. The electrolyte of most concern in wash water is calcium due to its high concentration in many aqueous media and its ability to exchange with the soluble sodium cation on sulfated surfactants to form an insoluble calcium salt of the sulfated surfactant, which precipitates out onto the substrate to be cleaned as a particle or film. The hardness of the water, or concentration of calcium and other electrolytes in water, will vary widely depending on the purification method and efficiency of water treatment plants which dispense water to the consumer of the detergent or cleaning composition. Accordingly, there remains a need to provide a surfactant which is tolerant to high concentrations of calcium so as to provide a cleanser which performs as expected in a wide variety of aqueous media.

Due to constraints on water consumption, especially in locations where the supply of drinking water to a population is limited, inadequate, or expensive, there is a desire to employ unprocessed or lightly processed water having a high concentration of saline as a wash media. In particular, there exists a need in some locations to use sea water or brackish water which is unprocessed or lightly processed as the aqueous media for many applications outside of drinking water, such as dishwashing and laundry water. The need to provide for a surfactant which is tolerant to high concentrations of electrolytes, such as calcium, is readily apparent if one must wash or clean a substrate in sea water or brackish water. Thus, there also exists a desire to find a surfactant composition, which is so highly tolerant to calcium that it is suitable for use in seawater or brackish as a cleansing agent.

It would also be desirable to manufacture a surfactant which can be easily and economically stored and transported. Polyoxyethylene nonionic linear alcohol surfactants, especially those containing from 3 or more ethylene oxide units, are solid or waxy products at ambient conditions (25° C. and 1 atm). Since these waxy or solid products cannot be pumped at ambient conditions, they must first be melted into the liquid phase and kept as a liquid during offloading and feeding into a reaction vessel or a blend tank. Further, the waxy and solid polyoxyethylene linear alcohols must be shipped and/or transported in drums, which take up more warehouse space than liquid storage tanks. It would be desirable to produce a polyoxyalkylene surfactant which is flowable and pumpable at ambient conditions, and yet more desirable to produce such an surfactant which is flowable and pumpable in cold climates where temperatures drop to 0° C.

SUMMARY OF THE INVENTION

A branched primary alcohol composition is provided comprising a branched ether primary alcohol represented by the formula

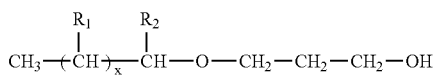

wherein $R_1$ represents hydrogen or a hydrocarbyl radical having from 1 to 3 carbon atoms, $R_2$ represents a hydrocarbyl radical having from 1 to 7 carbon atoms, x is a number ranging from 0 to 16, wherein the total number of carbon atoms in the alcohol ranges from 9 to 24.

There is also provided derivatives of the branched primary alcohol compositions such as alkoxylates, sulfates, and alkoxylsulfates of such alcohol compositions. The derivatives are useful as detergent compositions having cold water solubility and high tolerance to calcium.

DESCRIPTION OF THE PREFERRED EMBODIMENTS

It has now been found that a surfactant and a composition exhibiting high calcium tolerance can be provided using the composition of the invention containing derivatives of certain branched primary alcohol. It has been further found that the product has better cold water solubility than a linear alkyl sulfate having a comparable carbon number as measured by its Krafft point.

There is now provided a certain branched primary alcohol sulfate composition and a certain branched primary alcohol alkoxylsulfate composition having a calcium tolerance of 5000 ppm $CaCl_2$ or more, and as much as 50,000 or more, preferably, 20,000 $CaCl_2$ or more, more preferably 50,000 ppm or more, most preferably surfactant and a composition which possesses high calcium tolerance.

There is also provided a branched ether primary alcohol having a remote alpha branch ether trimethylene group, derivatives thereof such as alkoxylates (e.g., ethoxylates and/or propoxylates), the sulfates of each, and biodegradable branched ether surfactant compositions. The remote alpha branch ether trimethylene moiety is structurally represented as:

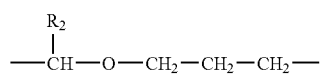

wherein $R_2$ represents a hydrocarbyl radical having from 1 to 7 carbon atoms, preferably 1 carbon atom.

The term "hydrocarbyl" as used herein means that the radical concerned is primarily composed of hydrogen and carbon atoms but does not exclude the presence of other atoms or groups in a proportion insufficient to detract from the substantially hydrocarbon characteristics of the radical concerned. Such radicals include:

(i) Hydrocarbon groups, for example, aliphatic (e.g., alkyl or alkenyl), alicyclic (e.g., cycloalkyl or cycloalkenyl) and aromatic groups, aromatic groups having aliphatic or alicyclic substituents, and aliphatic and alicyclic groups having aromatic substituents. Examples of hydrocarbon groups include methyl, ethyl, ethenyl, propyl, propenyl, butenyl, cyclohexyl, t-butylphenyl, 2-benzethyl and phenyl groups;

(ii) Substituted hydrocarbon groups, that is, groups having one or more non-hydrocarbon substituents which do not detract from the substantially hydrocarbon characteristics of the group. Examples of suitable non-hydrocarbon substituents include hydroxy, nitrile, nitro, oxo, chloro groups, and groups having ether or thioether linkages; and (iii) Hetero groups, that is, groups containing an atom other than carbon in a chain or ring otherwise composed of carbon atoms, the said atom not detracting from the substantially hydrocarbon characteristics of the group and inert to reactions.

Nitrogen, oxygen and sulphur may be mentioned as suitable hetero atoms. The hydrocarbyl radicals preferably contain only one non-hydrocarbon substituent or one non-carbon hetero atom if such substituents or atoms are present.

Anionic surfactants in detergent formulations are generally known to be subject to precipitation from wash water solutions containing hard water ions, e.g., magnesium and particularly calcium. Without intending to be bound by the theory, it is believed that the tolerance of the surfactant molecules of the invention, the compositions containing these molecules, and the formulations thereof, to calcium ions in wash solutions is attributable to the unique structure of the branched primary alcohol having a remote alpha branch ether trimethylene group.

The certain branched primary alcohol composition of the invention is represented by the formula:

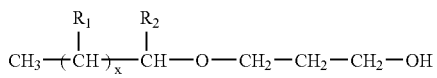

wherein $R_1$ represent hydrogen or a hydrocarbyl radical having from 1 to 3 carbon atoms, preferably hydrogen, $R_2$ represents a hydrocarbyl radical having from 1 to 7 carbon atoms, preferably 1 carbon atom, x is a number ranging from 0 to 16, preferably from 3 to 13, wherein the total number of carbon atoms in the alcohol ranges from 9 to 24, preferably from 9 to 20.

The branched ether surfactant of the invention is made by reacting an olefin with 1,3-propane diol in the presence of a suitable catalyst under primary alcohol forming conditions.

An olefin means any compound containing at least one carbon-carbon double bond. The desired average chain length of the olefin ranges from 3–18 aliphatic carbon atoms, preferably from 6–18, and more preferably from 12–16 aliphatic carbon since molecules within this range are used in many washing applications. The most suitable chain length, however, will depend upon the particular end use, such as dish washing, liquid hand soap, bar soap, laundry detergent, hard surface cleaners, or oil field applications.

The olefins may be linear or branched, may contain multiple double bonds anywhere along the chain, and may also contain acetylenic unsaturation. Further, the olefins may be substituted or unsubstituted, or may contain heteroatoms. The olefin may also be a bridged alpha olefin, such as a $C_1$–$C_9$ alkyl substituted norbornenes. Examples of norbornenes include 5-methyl-2-norbornene, 5-ethyl-2-norbornene, and 5-(2'-ethylhexyl)-2-norbornene.

The olefin may contain an aryl, alkaryl, or cycloaliphatic group along with an aliphatic moiety within the same olefin compound, or the olefin may consist solely of an aliphatic compound. Examples of aryl groups include phenyl, naphthyl, and the like. Examples of cycloaliphatic moieties include the cyclo propyls, butyls, hexyls, octyls, decyls, etc. Examples of alkaryls include tolyl, xylyl, ethylphenyl, diethylphenyl, and ethylnaphthyl. Preferably, the olefin composition comprises at least 90 wt. %, more preferably at least 95%, most preferably at least 98 wt. % aliphatic compounds.

The olefin may contain branched or linear olefins, or both. Examples of branching include alkyl, aryl, or alicyclic branches, preferably alkyl branches, and especially those alkyl groups having from 1 to 4 carbon atoms. The location of a branch on the olefin is not limited. Branches or functional groups may be located on the double bond carbon atoms, on carbon atoms adjacent to the double bond carbon atoms, or anywhere else along the carbon backbone.

The number of unsaturated bond sites along the chain is also not limited. The olefin may be a mono-, di-, tri-, etc. unsaturated olefin, optionally conjugated. The olefin may also contain acetylenic unsaturation. Preferably, the olefin composition comprises at least 90 wt. %, more preferably at least 95 wt. %, most preferably at least 98 wt. % mono-unsaturated olefin.

The olefin composition may comprise alpha olefins or internal olefins. An alpha olefin is an olefin whose double bond is located on both of α and β carbon atoms. An α carbon atom is any terminal carbon atom, regardless of how long the chain is relative to other chain lengths in a molecule. Specific non-limiting examples of alpha olefins suitable for use in the invention include 1-propylene, 1-butene, 1-pentene, 1-isopentene, 1-hexene, 2-methyl-1-hexene, 1-octene, 1-nonene, 1-decene, 1-undecene, 1-dodecene.

An internal olefin(s) is an olefin whose double bond is located anywhere along the carbon chain except at any terminal carbon atom.

The olefin composition feedstock is generally produced by commercial processes such as the oligomerization of ethylene, optionally followed by isomerization and disproportionation, such as those manufactured by Shell Chemical Company under the trademark NEODENE, or those manufactured by Chevron Chemical Company and BP-Amoco. Specific procedures for preparing suitable linear olefins from ethylene are described in U.S. Pat. Nos. 3,676,523, 3,686,351, 3,737,475, 3,825,615 and 4,020,121, the teachings of which are incorporated herein by reference. While most of such olefin products are comprised largely of alpha-olefins, higher linear internal olefins are also commercially produced, for example, by the chlorination dehydrochlorination of paraffins, by paraffin dehydrogenation, and by isomerization of alpha-olefins. Linear internal olefin products in the C6 to C18 range are marketed by Shell Chemical Company and by Chevron Company.

Alternatively, the olefin composition may be produced by the Fischer-Tropsch process, which typically contains a high proportion of paraffins. A Fischer-Tropsch process catalytically hydrogenates CO to produce compositions containing aliphatic molecular chains. Other processes for making feedstocks which may contain mixtures of olefins and paraffins include the dehydrogenation of paraffin, such as those made by the Pacol™ processes of UOP, and the cracking of paraffin waxes.

The olefin feedstock composition may be a processed stream that has been fractionated and/or purified by a conventional distillation, extraction, or other separation operation to obtain a desired carbon number cut. Such operation produce compositions containing a mixture of carbon numbers or a single carbon cut composition. In these feedstocks, a mixture of olefins having different carbon numbers within the stated range and outside of the stated range may be present. However, the average carbon number of the mixture of all olefins is within the stated range. The feedstock stream preferably contains an average aliphatic carbon number ranging from $C_6$–$C_{16}$, and more preferably ranging from $C_{12}$–$C_{16}$, and wherein the predominant olefin species is within these ranges, inclusive. In addition to mixtures of olefins within this range, one may also employ what are known as single carbon cuts of olefins as feedstocks, wherein the single cut is within this range. For example, the feedstock employed may be a single $C_6$, $C_8$, $C_9$, $C_{10}$, $C_{11}$, $C_{12}$, $C_{14}$, or $C_{16}$ carbon cut.

The most preferred olefin composition feedstock are those obtained from ethylene oligomerization and Fischer-Tropsch (FT) synthesis. In one embodiment, the feedstock used comprises an alpha olefin composition having at least 70 wt. % or more, more preferably at least 80 wt. % or more, most preferably at least 90 wt. % or more, of linear alpha mono-olefins within the desired carbon number range, (e.g., $C_6$, $C_{9-11}$, $C_{11-15}$, $C_{14-15}$, $C_{15-18}$, etc.), the remainder of the product being olefin of other carbon number or carbon structure, diolefins, paraffins, aromatics, and other impurities resulting from the synthesis process.

The catalyst used in the synthesis of the branched ether primary alcohol is preferably an acid catalyst. The acid catalyst is any conventional acidic catalyst effective to catalyze the reaction of the olefin with the diol to produce the branched alcohol surfactant of the invention. Conventional acidic catalysts include, broadly, the Bronsted acids, Lewis acids or Friedel-Crafts catalysts, zeolites, and ionic exchange resins. The catalyst may be homogeneous or heterogeneous in the reaction mixture of olefin, diol, and reaction product. The reactants may contact a heterogeneous catalyst in suspension or on a fixed bed.

Suitable Lewis Acids typically include the halides and alkyl compounds of the elements in Groups IV B to XVIII B and III A to VI A of the Periodic Table of the Elements. Examples of Lewis acids and Friedel-Crafts catalysts are the fluorides, chlorides, and bromides of boron, antimony, tungsten, iron, nickel, zinc, tin, aluminum, gallium, indium, zirconium, vanadium, bismuth, titanium and molybdenum. The use of complexes of such halides with, for example, alcohols, ethers, carboxylic acids, and amines are also suitable. More specific examples include $BF_3$, $BCl_3$, aluminum bromide, $FeCl_3$, $SnCl_4$, $SbCl_5$, $AsF_5$, $AsF_3$, $TiCl_4$, trimethyl aluminum, triethyl aluminum, and $AlR[n]X[3-n]$ wherein n is an integer from 0 to 3, R is C1–C12 alkyl or aryl, and X is a halide, for example, $Al(C_2H_5)_3$, $Al(C_2H_5)_2Cl$, $Al(C_2H_5)Cl_2$, and $AlCl_3$, titanium tetrachloride, zirconium tetrachloride, tin tetrachloride vanadium tetrachloride and antimony pentafluoride.

Specific examples of Bronsted acids include, but are not limited to, phosphoric acid, sulfuric acid, sulfur trioxide, sulfonic acid, boric acid, hydrofluoric acid, fluorosulfonic acid, trifluoromethanesulfonic acid, and dihydroxyfluoroboric acid, perchloric acid and the perchlorates of magnesium, calcium, manganese, nickel and zinc; metals oxalates, sulfates, phosphates, carboxylates and acetates; alkali metal fluoroborates, zinc titanate; and metal salts of benzene sulfonic acid.

Suitable organic sulfonic acids include the alkane and cycloalkane sulfonic acids, as well as arenesulfonic acids and heterocyclic sulfonic acids. Specific examples of the alkane sulfonic acids include methanesulfonic acid, ethanesulfonic acid, propanesulfonic acid, butanesulfonic acid, pentanesulfonic acid, hexanesulfonic acid, dodecanesulfonic acid, hexadecanesulfonic acid, trifluoromethane sulfonic acid, sulfosuccinic acid, and cyclohexylsulfonic acid. Specific examples of arenesulfonic acids include benzenesulfonic acid, toluenesulfonic acid, styrene-(i.e., vinyl benzene) sulfonic acid, 5-sulfosalicylic acid, phenolsulfonic acid, and 1,6-naphthalene disulfonic acid. Specific examples of heterocyclic sulfonic acids include sulfanilic acid. Alkyl and aryl groups of the sulfonic acid molecule are suitably substituted with relatively inert organic and/or inorganic substituents. Examples of substituted organic sulfonic acids include 4-hydroxybenzene sulfonic acid, trifluoromethane sulfonic acid, isethionic acid, and taurine.

A class of sulfur based acids commonly used in homogeneous acidic catalyzed reactions include sulfuric acid, sulfur trioxide, C1 to C30 alkyl sulfuric acids, sulfanilic acid, toluenesulfonic acid, styrenesulfonic acid, methanesulfonic acid, and 5-sulfosalicylic acid.

Also included as an acid catalyst are any of the alkoxylation catalysts, magnesium in combination with halides of aluminum, boron, zinc, titanium, silicon, or molybdenum; $BF_3$ or $SiF_4$ in combination with an alkyl or alkoxide compound of aluminum, gallium, indium, thallium, titanium, zirconium and hafnium; and a mixture of HF and one or more metal alkoxides.

Instead of an acidic homogeneous catalyst, one may also employ a solid acidic heterogeneous catalyst. Solid acidic catalysts include acidic polymeric resins, supported acids, and acidic inorganic oxides. The solid acidic catalysts have the advantage of avoiding the difficult separation steps for removing the catalyst from unreacted diol in the product mixture, and further avoid the need to deactivate the catalyst in the event that the catalyst is not removed from the product mixture. In one embodiment of the invention, the diol is pretreated to reduce the quantity of carbonyl compounds present as impurities in the diol composition prior to reaction with the olefin in the presence of a solid acidic heterogeneous catalyst, thereby extending the life of the solid acidic catalyst. Typical carbonyl impurities present in a diol include aldehydes or acetals. One example of a suitable pre-treatment is to hydrotreat the diol. Suitable hydrotreating methods include treatment with sodium borohydride or catalytic hydrogenation such as nickel on alumina or silica catalyst. In a more preferred embodiment, the amount of carbonyl impurities present in the diol is reduced to less than 100 ppm, more preferably to less than 50 ppm, most preferably to less than 10 ppm.

An example of a solid acidic polymeric resin is a solid acidic ion exchanger having acid active sites and a strong acid activity of each acid site. Common acidic ion exchange resins are sulfated resins, wherein the resins are copolymers of styrene and divinylbenzene, phenol based resins, poly (tetrafluoroethylene) polymers or siloxane polymers. Specific examples of such resins include the line of AMBERLYST® catalysts, including AMBERLYST® 15, 36 or 38, NAFION® or DELOXAN® catalysts. Other supported solid acidic catalysts include the Lewis acids (examples include $BF_3$, $BCl_3$, $AlCl_3$, $AlBr_3$, $FeCl_2$, $FeCl_3$, $ZnCl_2$, $SbF_5$, $SbCl_5$ and combinations of $AlCl_3$ and HCl) which are supported on solids such as silica, alumina, silica-aluminas, zirconium oxide or clays. When supported liquid acids are employed, the supported catalysts are typically prepared by combining the desired liquid acid with the desired support and drying. Supported catalysts which are prepared by combining a phosphoric acid or sulfur based acid with a support are low in cost.

Acidic inorganic oxides which are useful as catalysts include, but are not limited to, aluminas, silica-aluminas, aluminophosphates, natural and synthetic pillared clays, and natural and synthetic zeolites such as faujasites, mordenites, L, omega, X, Y, beta, ZSM, and MCM zeolites.

Representative examples of naturally occurring zeolites include faujasite, mordenite, zeolites of the chabazite-type such as erionite, offretite, gmelinite and ferrierite. Clay catalysts, another class of crystalline silicates, are hydrated aluminum silicates. Typical examples of suitable clays, which are acid-treated to increase their activity, are made from halloysites, kaolinites and bentonites composed of montmorillonite. These catalysts can be synthesized by known methods and are commercially available.

Suitable synthetic zeolites include ZSM -4 as described in U.S. Pat. No. 4,021,447, ZSM -5 as described in U.S. Pat. No. 3,702,886, ZSM -11 as described in U.S. Pat. No. 3,709,979, ZSM -12 as described in U.S. Pat. No. 3,832,449 and 4,482,531, ZSM -18 as described in U.S. Pat. No. 3,950,496, ZSM -20 as described in U.S. Pat. No. 3,972,983, ZSM -21 as described in U.S. Pat. No. 4,046,859, ZSM -25 as described in U.S. Pat. No. 4,247,416, ZSM -34 as described in U.S. Pat. No. 4,086,186, ZSM -38 as described in U.S. Pat. No. 4,046,859, ZSM -39 as described in U.S. Pat. No. 4,287,166 ZSM -43 as described in U.S. Pat. No. 4,247,728, ZSM -45 as described in U.S. Pat. No. 4,495,303, ZSM -48 as described in U.S. Pat. No. 4,397,827, ZSM -50 as described in U.S. Pat. No. 4,640,829, ZSM -51 as described in U.S. Pat. No. 4,568,654, ZSM -58 as described in U.S. Pat. No. 4,698,217, MCM -2 as described in U.S. Pat. No. 4,647,442, MCM -14 as described in U.S. Pat. No.

4,619,818, MCM -22 as described in U.S. Pat. No. 4,954,325, MCM -36, MCM -49 as described U.S. Pat. No. 5,236,575, MCM -56, SSZ-25, SSZ-31, SSZ-33, SSZ-35, SSZ-36, SSZ-37, SSZ-41, SSZ-42, beta as described in U.S. Pat. No. 3,308,069 and RE. 28,341, X as described in U.S. Pat. No. 3,058,805, Y as described in U.S. Pat. No. 3,130,007, and mordenite as described in U.S. Pat. No. 3,996,337, the entire contents of which are incorporated herein by reference. If desired, the zeolites can be incorporated into an inorganic oxide matrix material such as a silica-alumina.

Representative examples of useful silica alumina phosphate catalysts include SAPO-5, SAPO-11 and SAPO41 as described in U.S. Patent No. U.S. Pat. No. 4,440,871, incorporated herein by reference.

Intermediate pore size (up to 7.5 Angstroms in the largest dimension at the pore opening) and larger pore zeolites are preferred. Large pore size zeolites are most preferred because they can accommodate the larger olefin molecules, thereby providing a higher active surface area for reaction between the diols and olefins.

Examples of intermediate pore size zeolites include ZSM -5, ZSM -11, ZSM -12, ZSM -21, ZSM -22, ZSM -23, ZSM -35, ZSM -38, ZSM -48, ZSM -57, and ZSM -58.

Larger pore size zeolites include MCM -22, zeolite Beta, zeolite Y, ZSM -20, and the like. Examples of a preferred modified Y type zeolite include those disclosed in U.S. Pat. No. 5,059,567, which disclosure is hereby incorporated by reference.

Such zeolite catalyst should be at least partly in the acidic (H) form to confer the acidity for the reaction but may contain other cations such as ammonium ($NH4^+$).

The form and the particle size of the catalyst are not critical to the present invention and may vary depending, for example, on the type of reaction system employed. Non-limiting examples of the shapes of the catalyst in the present invention include balls, pebbles, spheres, extrudates, channeled monoliths, honeycombed monoliths, microspheres, pellets, or structural shapes, such as lobes, trilobes, quadralobes, pills, cakes, honeycombs, powders, granules, and the like, formed using conventional methods, such as extrusion or spray drying.

The diol and olefin react through the hydroxyl-double bond sites in the presence of an acidic catalyst to produce a branched primary alcohol ether surfactant of the invention containing within the molecule the remote alpha branch ether trimethylene moiety. For illustrative purposes, when the olefin is an alpha-olefin, the reaction proceeds according to the following equation:

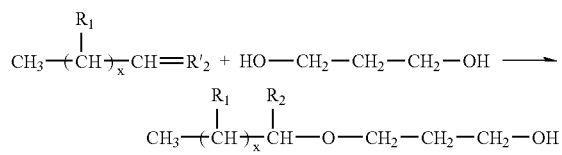

$R_1$ and $R_2$ represents the hydrocarbyl group as described above, and $R_2'$ is $R_2$ less hydrogen where the linkage with the CH group is by double bond and x is the same as described above. When the olefin is reacted with the diol, the hydroxyl hydrogen becomes bonded to the $R_2'$ to become $R_2$.

The products produced from the reaction of the olefin and diol compositions include the isomers of the olefin-diol adduct, olefin dimers, diolefin ether adducts, and diol dimers. Isomers of the olefin-diol adduct are made by reaction of the diol at the electropositive stable double bond carbon. In the presence of an acidic catalyst, double bond isomerization may occur, resulting in an product mixture which contains branches of different carbon number length depending upon the position of the double bond at the time the diol reacts with the olefin. To illustrate, the reaction of 1,3-propanediol with 1-dodecene in the presence of an acidic catalyst may produce the following isomers:

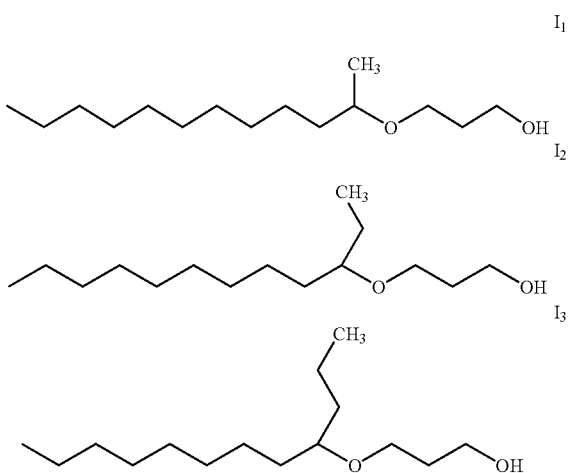

$I_1$ is made by the nucleophilic attack of the oxygen atom with an olefin when the double bond is in the alpha 1,2 carbon atom position. In this case, no double bond isomerization occurs, resulting in the desired product. $I_2$ is made when the olefinic double bond is isomerized to the 2,3 carbon atoms, and $I_3$ is made when the olefinic double bond is isomerized to the 3,4 carbon atoms. Double bond isomerization can be minimized by selection of an acidic catalyst which does not tend to double bond isomerize the olefin. Double bond isomerization may also be minimized by reducing the residence time of the diol-olefin reaction, and by carrying out the diol-olefin reaction at temperatures higher than typical temperatures favored for double bond isomerization. In general, double bond isomerization is favored at temperatures ranging from 50° C. to 150° C.

Another by-product, the diolefin ether adduct, is made when two olefin molecules react with diol across the diol hydroxyl groups. To illustrate, such a by-product is represented by the formula:

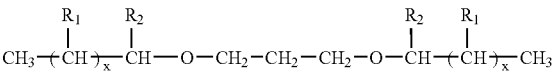

wherein $R_1$, $R_2$, and x is as described above. Formation of this by-product is minimized by using a molar excess of propanediol to olefins. While suitable molar ratios of diol to olefin range from 0.1:1 to 100:1, it is preferred to use a diol to olefin ratio of at least 1:1, more preferably from greater than 1:1, and most preferably at least 1.5:1. An alternative which simulates a molar excess of diol to olefin to obtain the same effect, the olefin may be slowly added over a period of time to the whole amount of diol to be reacted over a period to the diol to the olefin/catalyst mixture, having the effect of a large molar excess of diol.

Other by products which may be formed in the reaction of an olefin with a diol include the dimers of the olefins contained in the olefin composition, the dimers of the diols used in the diol composition.

The olefin-diol adducts of the invention are obtained in high purity. Based on the weight percentage of reaction products, the reaction of the olefin with diol in the presence of an acid catalyst, the selectivity of the olefin-diol product is 80 wt. % or more of the total reacted product mixture, more preferably 85 wt. % or more, most preferably 90 wt. % or more.

The process for making the branched ether surfactant compositions of the invention is flexible in that suitable product can be made under a wide range of operating conditions. The reaction temperature and pressure is not limited, so long as the reaction proceeds forward within the desired time and the product and reactants do not decompose. The reaction is carried out under conditions effective to react the olefin and diol to produce the branched primary alcohol composition of the invention. Suitable reaction temperatures range from 50° C. to 250° C., more preferably from 100° C. to 200° C. The system pressure may be sub-atmospheric, atmospheric, or super-atmospheric, depending upon the equipment design and process flow chosen. The residence time in batch operations ranges from 5 minutes to 3 hours.

In a homogeneous batch process, olefin, diol, and catalyst are added to a reaction vessel and heated. The order of addition is not limited, however, yield of the is increased by adding the diol to the olefin. Accordingly, in a preferred embodiment, olefin and catalyst are heated in a reaction vessel, and the diol is added to the heated olefin and catalyst in the reaction vessel.

Sulfation

Anionic surfactants useful in preparing detergents having calcium tolerance and have solubility in cold water include alkyl ether sulfates of the branched primary alcohol of the invention. These materials have the respective formulae $XOSO_3M$, wherein X is represented by the formula

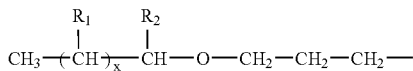

and M is hydrogen or a cation such as ammonium, alkanolammonium(e.g., triethanolammonium), a monovalent metal cation (e.g., sodium and potassium), or a polyvalent metal cation (e.g., magnesium and calcium). Preferably, M should be chosen such that the anionic surfactant component is water soluble.

The branched primary alcohol composition may be directly sulfated, or first alkoxylated followed by sulfation as described above. Alkoxylation of the branched primary alcohol is described below. The general class of alcohol alkoxysulfates can be characterized by the chemical formula:

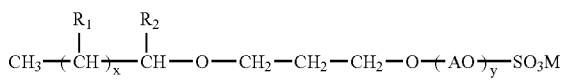

wherein $R_1$ represents hydrogen or a hydrocarbyl radical having from 1 to 3 carbon atoms, $R_2$ represents a hydrocarbyl radical having from 1 to 7 carbon atoms, x is a number ranging from 0 to 16, preferably from 3 to 13, A is an alkylene radical, preferably having carbon number in the range of 2 to 4, more preferably 2 or 3, most preferably 2, y is a number ranging from 1 to 9, wherein the total number of carbon atoms in the alcohol ranges from 9 to 24, and M is hydrogen or a cation described above. AO represent an oxyalkylene group.

The sulfating agents suitable for use in sulfating the branched primary alcohol or its alkoxylated derivative include those compounds capable of forming the carbon to oxygen to sulfur bonds necessary for the formation of an alkyl ether sulfate or alcohol alkyoxylsulfate. The particular sulfating agents used are typically a function of the compounds to be sulfated. These sulfating agents can be any sulfating agent known in the art for the sulfation of alcohols and include sulfur trioxide, chlorosulfonic acid or oleum.

Sulfation processes are described, for instance, in U.S. Pat. No. 3,462,525, issued Aug. 19, 1969 to Levinsky et. al., U.S. Pat. No. 3,428,654 issued Feb. 18, 1969 to Rubinfeld et. al., U.S. Pat. No. 3,420,875 issued Jan. 7, 1969 to DiSalvo et. al., U.S. Pat. No. 3,506,580 issued Apr. 14, 1970 to Rubinfeld et. al., U.S. Pat. No. 3,579,537 issued May 18, 1971 to Rubinfeld et. al., and U.S. Pat. No. 3,524,864 issued Aug. 18, 1970 to Rubinfeld, each incorporated herein by reference. Suitable sulfation procedures include sulfur trioxide ($SO_3$) sulfation, chlorosulfonic acid ($ClSO_3H$) sulfation and sulfamic acid ($NH_2SO_3H$) sulfation. When concentrated sulfuric acid is used to sulfate alcohols, the concentrated sulfuric acid is typically from about 75 percent by weight to about 100 percent by weight, preferably from about 85 percent by weight to about 98 percent by weight, in water. Suitable amounts of sulfuric acid are generally in the range of from about 0.3 mole to about 1.3 moles of sulfuric acid per mole alcohol, preferably from about 0.4 mole to about 1.0 mole of sulfuric acid per mole of alcohol.

A typical sulfur trioxide sulfation procedure includes contacting the branched primary alcohol or its alkoxylate and gaseous sulfur trioxide at about atmospheric pressure in the reaction zone of a falling film sulfator cooled by water at a temperature in the range of from about 25° C. to about 70° C. to yield the sulfuric acid ester of alcohol or its alkoxylate. The sulfuric acid ester of the alcohol or its alkoxylate then exits the falling film column and is neutralized with an alkali metal solution, e.g., sodium or potassium hydroxide, to form the alcohol sulfate salt or the alcohol alkoxylsulfate salt.

The sulfation reaction is suitably carried out at temperatures in the range of from about −20° C. to about 50° C., preferably from about 5° C. to about 40° C., and at pressures in the range of from about 1 atmosphere to about 5 atmospheres, preferably from about 1 atmosphere to about 2 atmospheres, and more preferably, about 1 atmosphere. Suitable residence times for the sulfation reaction range from a second to an hour, preferably from about 2 minutes to about 30 minutes.

The neutralization reaction is accomplished using one or more bases such as ammonium or alkali metal or alkaline earth metal hydroxides or carbonates or bicarbonates dispersed in a non-surfactant carrier. Suitable bases include sodium hydroxide, sodium carbonate, potassium hydroxide, calcium hydroxide and the like, with ammonium hydroxide, sodium hydroxide or potassium hydroxide being the preferred base. The amount of base added is in an amount sufficient and in a time sufficient to neutralize the acidity of the alkyl ether sulfonic acid.

The neutralization procedure can be carried out over a wide range of temperatures and pressures. Typically, the neutralization procedure is carried out at a temperature in the range of from about 0° C. to about 35° C., and typically at atmospheric pressure.

Alkoxylates

Alkoxylates of the branched primary alcohol of the inventions can be prepared by the sequential addition of alkylene oxide to the branched primary alcohol in the presence of a catalyst. Any known conventional alkoxylation method can be used.

The invention is preferably applied to processes utilizing an alkylene oxide (epoxide) reactant which comprises one or more vicinal alkylene oxides, particularly the lower alkylene oxides and more particularly those in the $C_2$ to $C_4$ range. In general, the alkylene oxides are represented by the formula

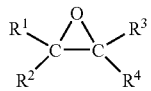

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide and propylene oxide. Alkylene oxide reactants consisting essentially of ethylene oxide are considered most preferred from the standpoint of commercial opportunities for the practice of alkoxylation processes, and also from the standpoint of the preparation of products having narrow-range ethylene oxide adduct distributions.

An illustration of the branched alkanol alkoxylate product of the invention by adding y numbers of alkylene oxide molecules to the to the branched primary alcohol of the invention is presented by the formula:

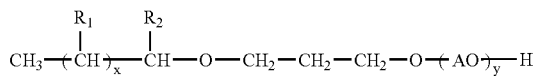

wherein $R_1$ represents hydrogen or a hydrocarbyl radical having from 1 to 3 carbon atoms, $R_2$ represents a hydrocarbyl radical having from 1 to 7 carbon atoms, x is a number ranging from 0 to 16, preferably from 3 to 13, A is an alkylene radical, preferably having carbon number in the range of 2 to 4, more preferably 2 or 3, most preferably 2, y is a number ranging from 1 to 9, wherein the total number of carbon atoms in the alcohol ranges from 9 to 24. AO represent an oxyalkylene group.

In terms of processing procedures, the alkoxylation reaction in the invention may be conducted in a generally conventional manner. For example, the catalyst in the liquid active hydrogen containing reactant is contacted, preferably under agitation, with alkylene oxide reactant, which is typically introduced in gaseous form, at least for the lower alkylene oxides.

In preferred embodiments, the alkylene oxide reactant is ethylene oxide or propylene oxide or a mixture of ethylene oxide and propylene oxide. The reaction is carried out in the presence of a catalytically effective amount of an alkoxylation catalyst. In a particularly preferred embodiment, ethylene oxide is contacted and reacted with the branched primary alcohol of the invention in the presence of a catalytically effective amount of a catalyst for aklkoxylation.

Any conventional alkoxylation catalyst can be used. One example of a typical catalyst is solid or aqueous solution of KOH. Examples of these catalyst can be found in U.S. Pat. No. 1,970,578 issued in 1934 and in C. Schoeller and M. Wittmer, German patent no. 605,973 which are herein incorporated by reference.

Another example of a suitable alkoxylation catalyst is described in U.S. Pat. No. 5,057,627 which is hereby incorporated by reference. Alkoxylation can be catalyzed by phosphate salts of the rare earth elements. These catalysts were typically prepared by adding an aqueous solution of a rare earth compound such as lanthanum chloride to an aqueous sodium orthophosphate or $H_3PO_4$ solution.

While these procedures describe a batch mode of operation, the invention is equally applicable to a continuous process.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reaction between the same reactants, employing conventional catalysts. A temperature of at least about 90° C., particularly at least about 120° C., and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Superatmospheric pressures, e.g., pressures between about 10 and 150 psig, are preferred, with pressure being sufficient to maintain the active hydrogen containing reactant substantially in the liquid state.

When the alkylene oxide reactant is a vapor, alkoxylation is then suitably conducted by introducing alkylene oxide into a pressure reactor containing the alcohol reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide is suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments, particularly for when the alkylene oxide is gaseous is less than 24 hours.

After the alkoxylation reaction has been completed, the product is preferably cooled. If desired, catalyst can be removed from the final product, although catalyst removal is not necessary to the process of the invention. Catalyst residues may be removed, for example, by filtration, precipitation, extraction, or the like. A number of specific chemical and physical treatment methods have been found to facilitate removal of catalyst residues from a liquid product. Such treatments include contact of the alkoxylation product with strong acids such as phosphoric and/or oxalic acids or with solid organic acids such as NAFION H+ or AMBERLITE IR 120H; contact with alkali metal carbonates and bicarbonates; contact with zeolites such as type Y zeolite or mordenite; or contact with certain clays. Typically, such treatments are followed by filtration or precipitation of the solids from the product. In many cases filtration, precipitation, centrifugation, or the like, is most efficient at elevated temperature.

The tolerance of the sulfated branched primary alcohols to calcium ions was determined by titration of test solutions of each of the compounds with calcium chloride. Specifically, the tolerance of the anionic surfactants to calcium ions was determined by taking ten (10) cc's of a 0.06% by weight anionic surfactant solution in distilled water adjusted to a pH of 5 using sodium hydroxide, added to a capped bottle, and placed into a oven maintained at 40° C. Addition of 10 micro liter aliquots of 10% solutions of calcium chloride in distilled water added to provoke a precipitate formation from the reaction of the surfactant and the salt. After a sufficient amount of time had elapsed for equilibration and phase separation, the clear, top, portion was measured for activity by/via the two phase titration method disclosed in Reid, V. W.,G. F. Longman and E. Heinerth, "Determination of Anionic-Active Detergents by Two-phase Titration," Tenside 4, 1967, 292–304. The reported calcium chloride tolerance is the ppm amount of calcium chloride which was added to precipitate fifty (50) weight % of the anionic surfactant.

The sulfated branched primary alcohol compositions of the invention have several orders of magnitude higher calcium tolerance over linear alkylbenzene sulfonates and branched alkyl sulfates having the same carbon number. In one embodiment, there is provided a sulfated branched primary alcohol composition and derivatives thereof having a calcium tolerance of 5000 ppm $CaCl_2$ or more. Preferably, the sulfated branched primary alcohol primary composition and derivatives thereof having a calcium tolerance of 20,000 $CaCl_2$ or more, more preferably 50,000 ppm or more, most preferably 75,000 or more, and even 100,000 ppm or more. By comparison, linear alkylbenzene sulfonates have calcium tolerance values under 250, linear alkylsulfates have calcium tolerance values under 100, and branched alkyl sulfates have calcium tolerance values under 500.

Such high calcium tolerance renders the surfactant compositions made by the branched primary alcohol compositions of the invention suitable for use in aqueous media having large levels of electrolytes. In one embodiment, there is provided a surfactant composition which is tolerant to aqueous media containing at least 100,000 ppm calcium chloride In another embodiment, there is provided a surfactant composition which is tolerant to sea water having a salinity of at least 25,000 ppm, preferably at least 30,000, more preferably about 34,000 ppm or more of total dissolved solids, and a cumulative amount of calcium and magnesium of at least 1000 ppm, more preferably at least 1500 ppm, most preferably at least 1700 ppm.

A useful test to determine whether a surfactant solution is tolerant to sea water is as follows: a 0.06% active surfactant solution in sea water is prepared and visually inspected for turbidity. The composition shown below, was visually observing whether any surfactant precipitates (fail) or whether no precipitation occurs (pass).

The sea water used for a test to determine whether a particular surfactant composition is tolerant to sea water has a composition of about 34 ppt salinity, with an ion concentration as follows:

| ION | Conc. (mg/l) |
|---|---|
| Chloride | 19251 |
| Sulfate | 2659 |
| Potassium | 402 |
| Carbonate/Bicarbonate | 192 |
| Boron | 5.6 |
| Iodide | 0.22 |
| Sodium | 10757 |
| Magnesium | 1317 |
| Calcium | 398 |
| Strontium | 8.6 |
| Bromide | 2.3 |
| Lithium | 0.18 |

Trace amounts of between 0.01 and 0.05 mg/l of each of copper, iron, nickel, zinc, maganese, molybdenum, cobalt, vanadium, aluminum, barium and fluorine are present. Other trace amounts of elements are be present in the following quantities:

Lead at <0.005 mg/l

Arsenic at <0.0002 mg/l

Chromium at <0.0006 mg/l

Trace amounts of Tin, Antimony, Rubidium and Selenium No or 0 amounts of Mercury, Nitrate and Phosphate.

In an independent embodiment of the invention, the branched ether surfactant compositions of the invention exhibit low Krafft temperature points. The Krafft temperature of anionic surfactants are measured by diluting the anionic surfactant to a homogeneous aqueous 1 weight % surfactant solution in water, freezing 25 cc aliquots of the solution in a freezer overnight at approximately −4 deg C. to force the surfactant out of solution, and then warming the solution in a temperature-controlled water bath in one degree intervals at a rate of one degree/hour. The reported Krafft temperature is the lowest temperature where the solution is fully transparent as determined by visual inspection.

In this embodiment, the sulfates of the branched ether primary alcohols, their derivatives, and their branched ether surfactant compositions exhibit Krafft temperatures of 10° C. or less, more preferably 0° C. or less. The branched ether surfactant compositions containing the sulfates of the branched ether primary alcohols and/or their derivatives are highly soluble in the aqueous wash media, thereby contributing to improved detergency performance and reducing the tendency toward precipitation, especially at colder wash temperatures of 50° F. (10° C.) or less.

In yet another independent embodiment of the invention, the branched ether surfactant compositions of the invention exhibit cold water detergency values of at least 22% measured at 50° F. (10° C.). In a preferred embodiment, the branched ether surfactant composition has a cold water detergency value of at least 28% measured at 50° F. In yet a more preferred embodiment, the sulfates of the branched ether primary alcohols, their derivatives, and their branched ether surfactant compositions simultaneously exhibit cold water detergency values of at least 22% at 50° F. (10° C.), Krafft temperatures of 10° C. or less, more preferably 0° C. or less, and has a calcium tolerance of 5000 ppm $CaCl_2$ or more.

The detergency evaluations can be conducted from a standard high density laundry powder (HDLP) Detergency/Soil Redeposition Performance test. The evaluations can be conducted using Shell Chemical Company's radiotracer techniques at 50° F. and 90° F. temperatures at a water hardness of 150 ppm as $CaCO_3$ ($CaCl_2/MgCl_2=3/2$ on a molar basis). The sulfated branched ether surfactant compositions of the invention can be tested, on a ¼ cup basis, against multisebum, cetanesqualane and clay soiled permanent press 65/35 polyester/cotton (PPPE/C) fabric. The HDLP's is tested at 0.74 g/l concentration, containing 27 wt % of the sulfated branched ether surfactant composition, 46 wt % of builder (zeolite-4A), and 27 wt % of sodium carbonate.

The composition of the radiolabeled Multisebum Soil is as follows:

| Component | Label | % wt. |
| --- | --- | --- |
| Cetane | 3H | 12.5 |
| Squalane | 3H | 12.5 |
| Trisearin | 3H | 10 |
| Arachis (Peanut) Oil | 3H | 20 |
| Cholesterol | 14C | 7 |
| Octadecanol | 14C | 8.0 |
| Oleic Acid | 14C | 15.0 |
| Stearic Acid | 14C | 15.0 |

A Terg-O-Tometer is used to wash the swatches at 15 minutes intervals. The wash conditions are set to measure both cold water detergency at 50° F. and warm water detergency at 90° F. The agitation speed is 100 rpm. Once the 4"×4" radiotracer soiled swatches are washed by the Terg-O-Tometer, they are hand rinsed. The wash and rinse waters are combined for counting to measure sebum soil removal. The swatches are counted to measure clay removal.

For details concerning the detergency methods and radiotracer techniques, reference may be had to B. E. Gordon, H. Roddewig and W. T. Shebs, HAOCS, 44:289 (1967), W. T. Shebs and B. E. Gordon, JAOCS, 45:377 (1968), and W. T. Shebs, Radioisotope Techniques in Detergency, Chapter 3, Marcel Dekker, New York (1987), each incorporated herein by reference.

The sulfates of the branched ether surfactant compositions of the invention are also biodegradable. The biodegradation testing methods for measuring the biodegradability of the sulfates can be conducted in accordance with the test methods established in 40 CFR §796.3200, also known as the OECD 301D test method, incorporated herein by reference. By a biodegradable composition or surfactant is meant that that the compound or composition gives a measured biochemical oxygen demand (BOD) of 60% or more within 28 days, and this level must be reached within 10 days of biodegradation exceeding 10 percent.

The Krafft point can be measured by preparing 650 ml of a 0.1% dispersion of glycasuccinimide in water by weight. If the surfactant was soluble at room temperature, the solution was slowly cooled to 0° C. If the surfactant did not precipitate out of solution, its Krafft point was considered to be <0° C. (less than zero). If the surfactant precipitated out of solution, the temperature at which precipitation occurs was taken as the Krafft point.

If the surfactant was insoluble at room temperature, the dispersion was slowly heated until the solution became homogeneous. It was then slowly cooled until precipitation occurred. The temperature at which the surfactant precipitates out of solution upon cooling was taken as the Krafft point.

Detergent Compositions

The sulfated branched primary alcohol or alcohol alkoxylsulfate composition of the invention find particular use in detergents, specifically laundry detergents. The alkoxylated branched primary alcohol composition of the invention also find particular use in detergents, specifically dishwashing detergents. Particularly, these alkoxylated branched primary alcohol composition of the invention have low odor compared with conventional detergent range alkoxylated alcohol composition currently available commercially. A biodegradable detergent composition can be prepared using the branched ether derivative compositions of the invention.

The detergent compositions are generally comprised of a number of components, besides the sulfated primary alcohol, alcohol alkoxylsulfate, or alkoxylated branched primary alcohol composition of the invention. The detergent composition may include: other surfactants of the ionic, nonionic, amphoteric or cationic type; builders (phosphates, zeolites), and optionally cobuilders (polycarboxylates); bleaching agents and their activators; foam controlling agents; enzymes; anti-greying agents; optical brighteners; and stabilizers.

Such additional detergent components useful for the invention are described in detail U.S. Pat. Nos. 6,087,311; 6,083,893; 6,159,920; 6,153,574; WO-A-9405761; and GB1429143. The disclosures are hereby incorporated by reference.

The following Examples are provided to further illustrate certain specific aspects of the invention but are not intended to limit its broader scope.

EXAMPLE 1

A reaction of 1-dodecene with 1,3-propanediol using a homogeneous acid catalyst, p-toluene sulfonic acid, to manufacture the surfactant of the invention is provided.

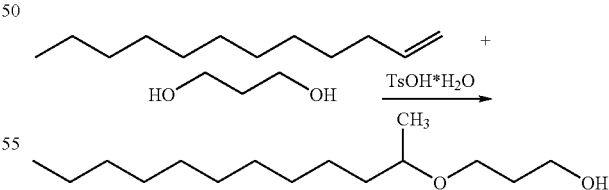

To a 500 ml round bottom flask equipped with an overhead stirrer, condenser and $N_2$ inlet system was added 100 grams (0.6 moles) of 1-dodecene (acquired from Aldrich Chemical Company) and 137 grams (1.8 moles) of 1,3-propanediol (obtained from Shell Chemical Company) and 4.56 grams (0.024 moles) of toluene sulfonic acid monohydrate. The mixture was heated to 150° C. for four hours at which time the reaction mixture was cooled to room temperature.

The reaction mixture consisted of two phases at room temperature. The two phases were separated by a separatory funnel. Each phase was analyzed by gas chromatography. 130 g of liquid were recovered in the top phase, and 107 g of liquid were recovered in the bottom phase. Analysis of the top phase indicated the formation of 24% wt of 3-dodecyloxy-1-propanol product, 72% wt unreacted dodecenes, 2% wt dodecene dimers and 2% wt 1,3-propanediol, didocecyl ether, based on the weight of the top phase liquid. There was less than 1% wt 1,3-propanediol or 1,3-propane diol oligomers in the top phase, indicating good phase separation. Analysis of the bottom phase indicated 94% wt unreacted 1,3-propanediol with about 6 wt % linear dimer of the propanediol, based on the weight of the bottom phase liquid. There was less than 1% wt dodecene or other dodecyl based adducts in the bottom phase, further confirming good phase separation between the product and unreacted olefin in the upper phase and the propane diol and dimers thereof in the lower phase.

Removal of the unreacted dodecenes in the upper phase by distillation afforded 29.5 grams of a mixture of isomers of 3-dodecyleneoxy-1-propanol. Selectivity to the 3-dodecyloxy-1-propanol product was 97%.

EXAMPLE 2

The reaction in example 1 was repeated using a lower quantity of 1,3-propanediol, and by adding the 1,3-propanediol to the 1-dodecene slowly during the reaction. To a 500 ml round bottom flask equipped with an overhead stirrer, condenser and $N_2$ inlet system was added 168 grams (1.0 mole) of 1-dodecene (acquired from Aldrich Chemical Company) and 2.25 grams(0.01 moles) of toluene sulfonic acid monohydrate. The mixture was heated to 150 C at which time 23 grams (0.3 moles) of 1,3-propanediol (obtained from Shell Chemical Company) was added slowly at the rate of 10 grams per hour. The reaction was stirred for an additional hour after the 1,3-propanediol had been added. The reaction mixture was cooled to room temperature.

The reaction mixture consisted of two discrete phases at room temperature. Dodecene was removed from the upper phase via distillation affording 15 grams of a clear oil. Analysis of this product mixture by gas chromatography indicated the formation of 74% wt 3-dodecyloxy-1-propanol, 24% wt of 1,3-propanediol, didodecyl ether and 2% wt dodecene dimer. Analysis of the bottom layer showed 98% wt unreacted 1,3-propanediol and 2% wt linear dimer of 1,3-propanediol (3-hydroxypropyleneoxy-1-propanol).

EXAMPLE 3

Addition of 1,3-propanediol to 1-dodecene is provided using another homogeneous catalyst, trifluoromethanesulfonic acid, as catalyst.

The reaction in example 2 was repeated using 1 gram (0.0067 moles) of trifluoromethanesulfonic acid as catalyst instead of p-toluenesulfonic acid. The reaction mixture was cooled to room temperature. The reaction mixture consisted of two phases. Dodecene was removed from the upper phase via distillation affording 23 grams of a clear oil. Analysis of this product mixture by gas chromatography indicated the formation of 69% w 3-dodecyloxy-1-propanol, 22% w of 1,3-propanediol, didodecyl ether and 9% w dodecene dimer. Analysis of the bottom layer showed 93% w unreacted 1,3-propanediol and 7% w linear dimer of 1,3-propanediol (3-hydroxypropyleneoxy-1-propanol).

EXAMPLE 4

Reaction of 1-dodecene with 1,3-propanediol is provided using a heterogeneous catalyst, beta $H^+$ zeolite as catalyst.

To a 500 ml round bottom flask equipped with an overhead stirrer, condenser and N2 inlet system was added 100 grams (0.6 moles) of 1-dodecene (acquired from Aldrich Chemical Company) and 137 grams (1.8 moles) of 1,3-propanediol (obtained from Shell Chemical Company) and 10 grams of beta zeolite powder, H+ form (obtained from Zeolyst Corporation). The mixture was heated to 150° C. for two hours at which time the reaction mixture was cooled to room temperature.

The reaction mixture consisted of two phases, with the powdered zeolite catalyst suspended in the bottom phase. The reaction mixture was diluted with 250 ml of heptane and 250 ml of distilled water, mixed well and the two phases separated using a separatory funnel. The top phase was isolated, and the heptane was removed by rotary evaporation affording 23.2 grams of clear oil.

Analysis of this product indicated the formation of 94% wt 3-dodecyloxy-1-propanol, 4% wt 3-dodecyoxypropyloxy-1-propanol and 2% w dodecene dimers. $C^{13}$ NMR analysis indicated that the 3-dodecyloxy-1-propanol was a mixture of isomers with 95% wt of the hydroxypropyl group attached at the 2-carbon position (relative to the alpha carbon atoms) of the dodecyl moiety to produce a methyl branched product ($I_1$) and 5% wt of the hydroxypropyl group attached at the 3-carbon position to produce an ethyl branched product ($I_2$). There was <1% w of attachment at the 4 ($I_3$) and the higher carbon positions. The isomers have the following structural formulas, respectively:

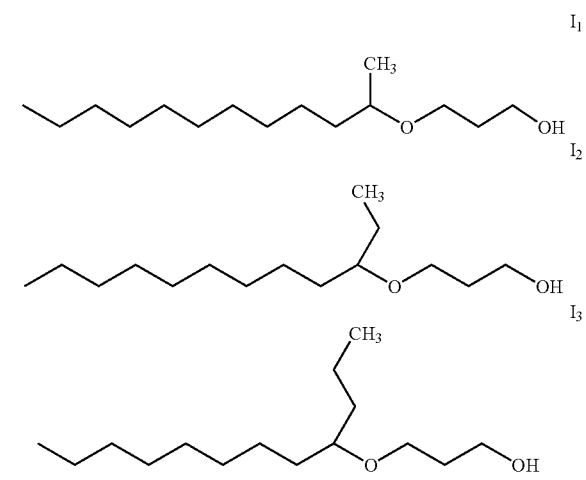

EXAMPLE 5

Reaction of NEODENE 14 Olefin (NEODENE is a trademark of Shell group of companies) with 1,3-propanediol using beta $H^+$ zeolite as catalyst is provided.

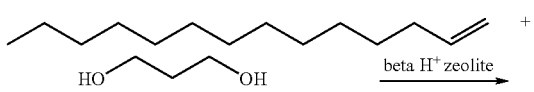

-continued

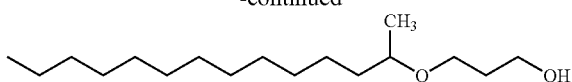

The reaction of Example 4 was repeated except that 118 grams (0.6 moles) of NEODENE 14 Olefin (1-tetradecene obtained from Shell Chemical Company) was used in place of 1-dodecene as the olefin. After the reaction mixture was cooled to room temperature, there resulted two discrete phases, each of which were analyzed by gas chromatography. The upper phase indicated the formation of 70% w unreacted tetradecenes, 27% w of isomers of 3-tetradecyloxy-1-propanol, ~3% w of the 3-tetradecyloxypropyloxy-1-propanol. Analysis of the bottom phase showed 94% w unreacted 1,3-propanediol, 5% w hydroxypropyloxy-1-propanol and a trace of higher trimer of 1,3-propanediol (i.e. oligomer).

EXAMPLE 6

Reaction of NEODENE 16 Olefin with 1,3-propanediol using beta Zeolite as Catalyst is provided.

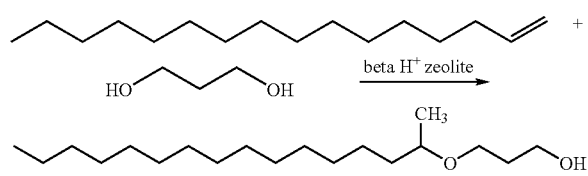

The reaction of Example 4 was repeated except that 135 grams (0.6 moles) of 16 Olefin (1-hexadecene obtained from Shell Chemical Company) was used in place of 1-dodecene as the olefin. After the reaction mixture was cooled to room temperature, both phases from the product mixture were analyzed by gas chromatography. The upper phase indicated the formation of 72% w hexadecenes, 25% w of isomers of 3-hexadecyloxy-1-propanol, ~3% w of the 3-hexadecyloxypropyloxy-1-propanol. Analysis of the bottom phase showed 96% w unreacted 1,3-propanediol, 4% w hydroxypropyloxy-1-propanol and a trace of higher trimer of 1,3-propanediol (i.e. oligomer).

EXAMPLE 7

Reaction of NEODENE 12 Olefin with 1,3-propanediol using another heterogeneous catalyst, CBV-500 Zeolite, as the catalyst is provided.

The reaction of Example 4 was repeated except that 100 grams (0.6 moles) of NEODENE® 12 Olefin (1-dodecene obtained from Shell Chemical Company) was used in place of 1-dodecene as the olefin and 10 grams of CBV-500 zeolite as catalyst. CBV-500 zeolite is a Y-type zeolite obtained from Zeolyst International. After about 3.5 hours of reaction time, the reaction mixture was cooled to room temperature, and both phases from the product mixture were analyzed by gas chromatography. The upper phase indicated the formation of 90% w unreacted dodecenes, 9% w of isomers of 3-dodecyloxy-1-propanol product, and trace amounts of the 3-dodecyloxypropyloxy-1-propanol. Analysis of the bottom phase showed 98% w unreacted 1,3-propanediol and 2% w 3-hydroxypropyloxy-1-propanol.

EXAMPLE 8

A reaction of NEODENE 12 Olefin with 1,3-propanediol using another heterogeneous catalyst, CBV-780 Zeolite as Catalyst is provided.

The reaction of Example 4 was repeated except that 100 grams (0.6 moles) of NEODENE 12 Olefin (1-dodecene obtained from Shell Chemical Company) was used in place of 1-dodecene as the olefin and 10 grams of CBV-780 Zeolite as catalyst. This catalyst is a modified Y-type zeolite obtained Zeolyst International. After the reaction mixture was cooled to room temperature, both phases from the product mixture were analyzed by gas chromatography. The upper phase indicated the formation of 90% w dodecenes, 9% w of isomers of 3-dodecyloxy-1-propanol product, and trace amounts of the 3-dodecyloxypropyloxy-1-propanol. Analysis of the bottom phase showed 98% w unreacted 1,3-propanediol and 2% w 3-hydroxypropyloxy-1-propanol.

EXAMPLE 9

A reaction of NEODENE 12 Olefin with 1,3-propanediol using another heterogeneous catalyst, CBV-740 Zeolite as Catalyst is provided.

The reaction of Example 4 was repeated except that 100 grams (0.6 moles) of NEODENE 12 Olefin (1-dodecene obtained from Shell Chemical Company) was used in place of 1-dodecene as the olefin and 10 grams of CBV-740 Zeolite as catalyst. CBV-740 zeolite is a modified Y-zeolite obtained from Zeolyst International. After the reaction mixture was cooled to room temperature, both phases from the product mixture were analyzed by gas chromatography. The upper phase indicated the formation of 91% w dodecenes, 8% w of isomers of 3-dodecyloxy-1-propanol product, and trace amounts of the 3-dodecyloxypropyloxy-1-propanol. Analysis of the bottom phase showed 98% w unreacted 1,3-propanediol and 2% w 3-hydroxypropyloxy-1-propanol.

EXAMPLE 10

A reaction of NEODENE 12 Olefin with 1,3-propanediol using another heterogeneous catalyst, 13× Molecular Sieve as Catalyst is provided.

The reaction of Example 4 was repeated except that 100 grams (0.6 moles) of NEODENE 12 Olefin (1-dodecene obtained from Shell Chemical Company) was used in place of 1-dodecene as the olefin and 10 grams of 13× Molecular Sieve obtained from PQ Corporation as catalyst. After the reaction mixture was cooled to room temperature, both phases from the product mixture were analyzed by gas chromatography. The upper phase indicated the formation of 82% w dodecenes, 16% w of isomers of 3-dodecyloxy-1-propanol product, and 2% w of the 3-dodecyloxypropyloxy-1-propanol. Analysis of the bottom phase showed 96% w unreacted 1,3-propanediol and 4% w 3-hydroxypropyloxy-1-propanol.

EXAMPLE 11

A reaction of NEODENE 12 Olefin with 1,3-propanediol using another heterogeneous catalyst, a $H^+$ Y Zeolite as Catalyst is provided.

The reaction of Example 4 was repeated except that 100 grams (0.6 moles) of NEODENE® 12 Olefin (1-dodecene obtained from Shell Chemical Company) was used in place of 1-dodecene as the olefin and 10 grams of $H^+$ Y Zeolite prepared by treatment of a Na—Y Zeolite(CBV-100 obtained from Zeolyst International) with ammonium nitrate followed by calcination at 500° C. in air for 8 hours was used as the catalyst. After the reaction mixture was cooled to room temperature, both phases from the product mixture were analyzed by gas chromatography. The upper phase indicated the formation of 94% w dodecenes and 6% w of isomers of 3-dodecyloxy-1-propanol product. No appreciable 3-dodecyloxypropyloxy-1-propanol was observed. Analysis of the bottom phase showed 96% w unreacted 1,3-propanediol and 4% w 3-hydroxypropyloxy-1-propanol.

EXAMPLE 12

A reaction of C15/C16 internal olefins with 1,3-propanediol (PDO) using a homogeneous catalyst, p-toluenesulfonic acid, is provided.

To a 500 ml Zipperclave autoclave was added 44 grams (0.2 moles) of a mixture of C15/C16 internal olefins obtained from Shell Chemical Company, 76 grams (1 mole) of 1,3-propanediol (acquired from Shell Chemical Company) and 0.38 grams (0.002 moles) of p-toluene sulfonic acid in 100 ml of tetrahydrofuran. The autoclave system was placed under N2 atmosphere after removal of air by repeated pressurization and depressurization with $N_2$. Then the pressure of the Zipperclave was adjusted to 50 psig $N_2$. The reaction was heated to 100° C. for 18 hours. The reaction was cooled to 25° C. The tetrahydrofuran solvent was removed by rotary evaporation producing two phases. The two phases were separated by separatory funnel.

Each phase was analyzed by gas chromatography. The upper phase indicated the formation of about 6% wt of the 1,3-propanediol adduct of the mixture of C15/C16 olefins. The balance was isomerized C15/C16 olefins. The lower phase consisted of 98% wt 1,3-propanediol and 2% wt 3-hydroxypropyl-1-propanol.

EXAMPLE 13

A reaction of C15/C16 internal olefins with PDO using p-toluenesulfonic acid as catalyst.

Example 12 was repeated except that 88 grams (0.4 moles) of a mixture of an internal C15/C16 olefin mixture obtained from Shell Chemical Company and 100 ml of dimethoxyethane was used as solvent. After the reaction was cooled to 25 C. the dimethoxyethane solvent was removed by rotary evaporation producing two phases. The phases were separated by separatory funnel. Each phase was analyzed by gas chromatography. The upper phase indicated the formation of ~8% w of the 1,3-propanediol adduct of the mixture of C15/C16 olefins. The balance was isomerized C15/C16 olefins. The lower phase consisted of 98% w 1,3-propanedioll and 2% w 3-hydroxypropyl-1-propanol.

EXAMPLE 14

A reaction of isomerized C15/C16 Olefins obtained from Shell Chemical Company with PDO using a homogeneous catalyst, trifluoromethane sulfonic acid is provided.

Example 13 was repeated except 0.3 grams (0.002 moles) of trifluoromethanesulfonic acid was used as catalyst. After the reaction was cooled to 25 C. The dimethoxyethane solvent was removed by rotary evaporation producing two phases. Each phase was analyzed by gas chromatography.

The upper phase indicated the formation of ~15% w of the 1,3-propanediol adduct of the mixture of C15/C16 olefins and 2% w of the hydroxypropoxypropyloxy adduct of the mixture of C15/C16 olefins. The balance was isomerized C15/C16 olefins. The lower phase consisted of 98% w 1,3-propanediol and 2% w 3-hydroxypropyl-1-propanol.

EXAMPLE 15

A reaction of 1-Dodecene with 1,3-propanediol using p-toluenesulfonic acid as catalyst and dimethoxyethane as solvent is provided.

To a 500 ml Zipperclave autoclave was added 67.2 grams (0.4 moles) of 1-dodecene [acquired from Aldrich Chemical Company], 76 grams (1 mole) of 1,3-propanediol [acquired from Shell Chemical Company] and 0.38 grams (0.002 moles) of p-toluene sulfonic acid in 100 ml of dimethoxyethane. The autoclave system was placed under $N_2$ atmosphere after removal of air by repeated pressurization and depressurization with $N_2$. Then the pressure of the Zipperclave was adjusted to 50 psig $N_2$. The reaction was heated to 150° C. for 3 hours. The reaction was cooled to 25° C. The dimethoxyethane solvent was removed by rotary evaporation producing two phases. Each phase was analyzed by gas chromatography. The upper phase indicated the formation of ~11% w of 3-dodecyloxy-1-propanol and 89% w mixed dodecenes. The lower phase consisted of 97% w 1,3-propanediol and 3% w 3-hydroxypropyl-1-propanol.

EXAMPLE 16

A Reaction of 1-Dodecene with 1,3-propanediol using trifluoromethanesulfonic acid as catalyst and dimethoxyethane solvent is provided.

Example 14 was repeated using 0.3 grams (0.002 moles) of trifluoromethanesulfonic acid as catalyst. The reaction was cooled to 25 C. The dimethoxyethane solvent was removed by rotary evaporation producing two phases. The dodecene was removed from the upper phase by distillation affording 2.3 grams of clear oil. Analysis indicated this product to be 3-dodecyloxy-1-propanol.

EXAMPLE 17

A reaction of 1-Dodecene with 1,3-propanediol using trifluoromethanesulfonic acid as catalyst without a solvent is provided.

Example 14 was repeated using 0.3 grams (0.002 moles) of trifluoromethanesulfonic acid as catalyst but no solvent. The reaction was cooled to 25 C. producing two phases. The dodecene was removed from the upper phase by distillation affording 9.4 grams of clear oil. Analysis indicated this product to be 3-dodecyloxy-1-propanol.

EXAMPLE 18

A Reaction of NEODENE 12 Olefin with PDO using a heterogeneous catalyst, CBV-500 Zeolite as catalyst is provided.

To a 500 ml round bottom flask equipped with an overhead stirrer, condenser and $N_2$ inlet system was added 100 grams (0.6 moles) of NEODENE 12 Olefin (obtained from Shell Chemical Company) and 137 grams (1.8 moles) of 1,3-propanediol (obtained from Shell Chemical Company) and 10 grams of CBV-500 Zeolite, a Y zeolite obtained from Zeolyst International. The mixture was heated to 150° C. for two hours at which time the reaction mixture was cooled to room temperature. The reaction mixture consisted to two phases and each phase was analyzed by gas chromatography. Analysis of the top phase indicated the formation of 4% w of 3-dodecyloxy-1-propanol and 96% w mixed dodecenes. Analysis of the bottom phase indicated 99% wt unreacted 1,3-propanediol with ~1% wt linear dimer.

EXAMPLE 19

A reaction of NEODENE 12 Olefin with PDO using another heterogeneous catalyst, CBV-712 Zeolite is provided.

Example 18 was repeated using 10 grams of CBV-712 Zeolite as catalyst. CBV-712 zeolite is a modified Y-zeolite obtained from Zeolyst International. Analysis of the top phase indicated the formation of 3% w of 3-dodecyloxy-1-propanol and 97% w mixed dodecenes. Analysis of the bottom phase indicated 99% wt unreacted 1,3-propanediol with ~1% wt linear dimer

EXAMPLE 20

Experiments were conducted using a fixed bed reactor system consisting of a 20 mm×220 mm 316 stainless steel tubular reactor which was fitted with a thermowell transversing the center of the tube and containing three temperature control/indicator thermocouples at the top, middle and bottom of the reactor. The tube was filled with 20 ml of CP861E beta zeolite extrudate obtained from Zeolyst International which had been calcined at 500° C. for 6 hours. The catalyst system was purged with $N_2$. NEODENE 12 Olefin and 1,3-propanediol were pumped separately to the reactor system at 20 ml/hr each initially at 25° C. and 1 atmosphere of $N_2$. The reactor system was heated to 150° C. and pumping continued for 8 hours. The product mixture separated into two clear, colorless phases at 25° C. and was analyzed by gas chromatography. Analysis of the upper phase showed the formation of 21% w 3-(2-methylundecyloxy)-1-propanol, 4% w 3-(2-ethyldecyloxy)-1-propanol and ~1% dodecene dimers. The remainder was a mixture of dodecenes. The lower phase contained 94% w unreacted 1,3-propanediol and 6% w linear dimer of PDO.

EXAMPLE 21

A larger scale reaction of NEODENE 12 Olefin with PDO Using beta H+ Zeolite Catalyst is provided.

A total of 2352 grams (14 moles) of NEODENE 12 Olefin obtained from Shell Chemical Company, 3192 grams (42 moles) of 1,3-propanediol and 200 grams of beta H+ Zeolite obtained from Zeolyst International were added to a 12 liter resin vessel fitted with overhead stirrer, thermowell, condenser and $N_2$ gas inlet/outlet system. The mixture was mixed well and heated to 150° C. for 5 hours. The reaction mixture was cooled to 25° C., resulting in the formation of two phases. The two phases were separated by separatory funnel. Each phase was analyzed by gas chromatography. Analysis of the top phase indicated the formation of 25.2% w of the 1-PDO adduct of NEODENE 12 Olefin, 2.0% w of the linear di-PDO adduct of NEODENE 12 Olefin, 4.4% w dodecene dimers and 68.4% w isomerized dodecenes. Analysis of the bottom phase indicated 90% w unreacted 1,3-propanediol, and 10% w linear di-PDO dimer. Distillation of the dodecenes from the upper phase afforded 858 grams of a clear, fluid liquid. Analysis of this material by $C^{13}$ NMR indicated the formation of 94% of the 1-PDO adduct of NEODENE 12 Olefin (of which 95% w was 3-(2-methylundecyloxy)-1-propanol and 5% w was 3-(3-ethyldecyloxy)-1-propanol) and 6% w was the linear PDO dimer (or PDO-2) adduct of NEODENE 12 Olefin.

EXAMPLE A–C

Examples of sulfated products derived from $C_{12}$, $C_{14}$, and $C_{16}$ branched primary alcohols, prepared in a manner similar to Example 6, respectively Examples A, B, and C, were produced according to the following method.

0.666 moles of the respective branched primary alcohol were dissolved in 300 mls of methylene chloride in a 500 ml multineck round bottom flask equipped with an addition funnel and stirring bar. The reaction mixture was cool to 0° C. 0.7 moles of chlorosulfonic acid was transferred to the addition funnel and added dropwise over a 15 minute period. The product was neutralized by pouring the reaction mixture into a well stirred aqueous solution of 0.7 moles of sodium hydroxide dissolved in approximately 800 mls of distilled water. The methylene chloride was removed from the mixture by reduced pressure. This produced an approximately 25 weight percent active solution of the desired sulfated products of the branched primary alcohols. The products were all clear fluid pale yellow liquids. Example A is $C_{12}$-1 PDOS. Example B is $C_{14}$-1 PDOS. Example C is $C_{16}$-1 PDOS.

For comparison, the properties of a primary alcohol sulfate produced by sulfation of NEODOL 23 Alcohol (mixture of $C_{12}$ and $C_{13}$ having typical hydroxyl number of 289 mg/gKOH) in a similar manner to those above obtained from Shell Chemical Co. and Witconate 1260, a 60% aqueous solution of $C_{12}$ linear alkyl sulfate ($C_{12}$ LAS) from Witco Corp. are provided.

| | RELATIVE STRENGTHS | | | | |
|---|---|---|---|---|---|
| Physical Property Attributes | $C_{12}$ LAS | N23-S | $C_{12}$ – 1 PDOS | $C_{14}$ – 1 PDOS | $C_{16}$ – 1 PDOS |
| Solubility ° C. | (+) | (−) | (+) | (+) | (−) |
| Critical Micelle Conc. (CMC) @ 25° C. | (−) | (−) | (+) | (+) | (++) |
| Hardness Tolerance $Ca^{++}$ | (−) | (−) | (+++) | (++) | (+) |
| Interfacial Tension 4/1 Cetane/oleic acid | (++) | (++) | (−) | (−) | (+) |
| Interfacial Tension Hexadecane | (+) | (+) | (−) | (−) | (+) |
| Other IFT in Seawater 4/1 above | (−) | None | (+) | (+) | (+) |
| Solubility in Seawater | (−) | (−) | (+) | (+) | (−) |

| Physical Property Attributes | ACTUAL VALUES | | | | |
|---|---|---|---|---|---|
| | $C_{12}$ LAS | N23-S | $C_{12}-1$ PDOS | $C_{14}-1$ PDOS | $C_{16}-1$ PDOS |
| Solubility ° C. Krafft 1.0% Solution | 0 | 29 | 0 | 0 | 22 |
| Critical Micelle Conc. (CMC) @ 25° C. | 0.070 Wt % | 0.140 Wt % | 0.062 Wt % | 0.029 Wt % | 0.0063 Wt % |
| Surface Tension (Dynes/Cm.) @ CMC | 34 | 25 | 28 | 30 | 33 |
| Foam Rate (cc/min) | 110 | 100 | 100 | 133 | 102 |
| Foaming Stability* | 14 | 20 | 10 | 14 | 16 |
| Hardness Tolerance $Ca^{++}$ | 140 ppm | 18 ppm | >120,000 ppm | 30,200 ppm | 1,800 ppm |
| Interfacial Tension 4/1 Cetane/oleic acid | 0.5 | 0.5 | 5.3 | 2.5 | 1.4 |
| Interfacial Tension Hexadecane☆ | 6.4 | 5.7 | 13.6 | 9.3 | 6.3 |
| Other IFT in Seawater 4/1 above | 0.5 | None | 0.12 | 0.11 | 0.17 |
| Solubility in Seawater❖ | Cloudy Ppt. | Cloudy Ppt. | Clear | Clear | Cloudy Ppt. |

*Centimeter of foam remaining after 20 minutes in DI water @ 25° C. and 0 ppm hardness.
☆Average Dynes/Centimeter in 0.1% solution at 25° C. over more than one hour.
❖Seawater is 3.589% synthetic salt that contains every major, minor and trace element found in original seawater. Parts per million concentration, ppm, is 35,890 ppm.

EXAMPLE D–F

Examples of ethoxylated products derived from $C_{12}$, $C_{14}$, and $C_{16}$ branched primary alcohols, prepared in a manner similar to Example 6, respectively Examples D, E, and F, were produced according to the following method.

7 moles of Ethylene oxide was introduced into a pressure reactor containing 1 mole the respective branched primary alcohol reactant and KOH as catalyst at a partial pressure of 30 psig and diluted with Nitrogen gas to a total pressure of 60 psig. The reaction was carried out at a temperature of 160° C. for a period of 2 hours. The ethylene oxide-alcohol adduct produced had an average 7 EO repeating units.

For comparison, the properties of an alcohol ethoxylate having an average of 7 ethoxylate repeat units prepared by ethoxylation of NEODOL 25 alcohol obtained from Shell Chemical Co. is provided.

Cloud point and phase behavior was measured as follows: A temperature scan is normally completed on a 1% solution of a nonionic alcohol ethoxylate to first determine the exact cloud point and secondly to determine the other phases that are inherent to the alcohol ethoxylate. This is accomplished by use of the dipping probe instrument, which measures the turbidity change in the ethoxylate as the temperature is increased from room temperature to ninety (90)° C. Each surfactant will have its own unique trace or "fingerprint" as the changes of temperature and turbidity are recorded and noted.

The solubilization rates of hexadecane and 4/1 hexadecane/oleic acid into 1% solutions were measured at 25° C. using the dipping probe colorimeter system. Hexadecane models a nonpolar lubricating oil while 4/1 hexadecane/oleic acid models a polar sebum-like soil. The rates were calculated by measuring the time required for 10 μl samples of oil to completely dissolve into the well-stirred solution as indicated by the disappearance of turbidity. The results for 4/1 hexadecane/oleic acid are given as an average value for five sequential injections while the data for hexadecane are based on a single injection.

As shown in the data table, the 7-EO PDO adduct provided faster solubilization on average than the commercial 7-EO ethoxylate having the same cloud point temperature. This result was true for both the nonpolar hexadecane oil as well as the nonpolar/polar oil blend containing oleic acid. Rapid solubilization of oil is indicative of good-cleaning surfactant systems that provide enhanced removal rates of oily soils from various solid substrates.

| Physical Property Attributes | ACTUAL VALUES | | | |
|---|---|---|---|---|
| | N25-7 | $C_{12}-1$ PDO 7EO | $C_{14}-1$ PDO 7EO | $C_{16}-1$ PDO 7EO |
| Cloud Point | | | | |
| UP (° C.) | 52.6 | 53.6 | 47 | 42.7 |
| DOWN (° C.) | 53.4 | 53.7 | 47.7 | 43 |
| AVERAGE (° C.) | 53.0 | 53.7 | 47.4 | 42.9 |
| L α Phase (° C. range) | 91–86 | 72.6–79 | 71–82 | Short @ 70~80 |
| L Phase (° C. range) | — | 83–85.9 | 86.5–88.4 | double |
| $L_2$ Phase (° C. range) | — | — | — | cloud |
| Solubilizations* (μL/minute) 4/1 Hexadecane/ oleic acid | | | | |
| 10 μL | 50.0 | 200.0 | 26.7 | 0.2 |
| 10 μL | 40.0 | 66.7 | 20.0 | 0.2 |
| 10 μL | 28.6 | 40.0 | 20.0 | None |
| 10 μL | 28.6 | 28.6 | 33.3 | None |
| 10 μL | 20.0 | 20.0 | 11.4 | None |

-continued

ACTUAL VALUES

| Physical Property Attributes | N25-7 | $C_{12}-1$ PDO 7EO | $C_{14}-1$ PDO 7EO | $C_{16}-1$ PDO 7EO |
|---|---|---|---|---|
| Average Hexadecane | 33.4 | 71.1 | 22.3 | 0.2 |
| 10 μL | 0.083 | 0.333 | 0.089 | 0.064 |
| 10 μL | None | None | None | None |
| 10 μL | None | None | None | None |

*25° C. Solubility

Solubility Key

| Result | Time, Min. | Seconds |
|---|---|---|
| 100 | 0.1 | 6 |
| 50 | 0.2 | 12 |
| 5 | 2 | 120 |
| 0.5 | 20 | 1200 |
| 0.05 | 200 | 12000 |

We claim:

1. A process to produce a branched alkyl ether sulfate composition comprising:
   a) contacting an olefin composition having an average carbon number in the range of 3 to 18 having the formula

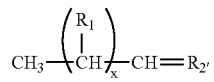

where $R_1$ represents hydrogen or a hydrocarbyl group having from 1 to 3 carbon atoms, $R_{2'}$ represents a hydrocarbyl group having from 1 to 7 carbon atoms where the linkage with the CH group is by double bond, and x is a number ranging from 0 to 16, with 1,3-propane diol in the presence of a catalyst effective to react the olefin with the diol under conditions effective to produce the branched alcohol composition; and
   b) contacting the branched alcohol composition with a sulfating agent under conditions effective to produce a branched alkyl ether sulfate composition.

* * * * *